(12) United States Patent
Kusumegi et al.

(10) Patent No.: US 9,005,920 B2
(45) Date of Patent: Apr. 14, 2015

(54) SOLUTION FOR CELL-FREE PROTEIN SYNTHESIS, KIT FOR CELL-FREE PROTEIN SYNTHESIS, AND METHOD OF PROTEIN SYNTHESIS

(75) Inventors: Takahiro Kusumegi, Miyoshi (JP); Toshiya Kawaguchi, Aichi-gun (JP)

(73) Assignee: Toyota Jidosha Kabushiki Kaisha, Aichi-ken (JP)

( * ) Notice: Subject to any disclaimer, the term of this patent is extended or adjusted under 35 U.S.C. 154(b) by 337 days.

(21) Appl. No.: 13/378,313

(22) PCT Filed: Jun. 15, 2010

(86) PCT No.: PCT/JP2010/060112
§ 371 (c)(1), (2), (4) Date: Dec. 14, 2011

(87) PCT Pub. No.: WO2010/147111
PCT Pub. Date: Dec. 23, 2010

(65) Prior Publication Data
US 2012/0088269 A1 Apr. 12, 2012

(30) Foreign Application Priority Data
Jun. 15, 2009 (JP) .................................. 2009-142368

(51) Int. Cl.
*C12P 21/06* (2006.01)
*C12P 21/02* (2006.01)

(52) U.S. Cl.
CPC ...................................... *C12P 21/02* (2013.01)

(58) Field of Classification Search
USPC ....................................................... 435/68.1
See application file for complete search history.

(56) References Cited

U.S. PATENT DOCUMENTS

| | | | |
|---|---|---|---|
| 5,545,539 A | 8/1996 | Miller | |
| 6,207,378 B1 | 3/2001 | Yamane et al. | |
| 2003/0113835 A1 | 6/2003 | Imamura et al. | |
| 2005/0069887 A1 | 3/2005 | Kitabayashi et al. | |
| 2005/0255542 A1* | 11/2005 | Shirouzu et al. | 435/68.1 |
| 2006/0211083 A1* | 9/2006 | Katzen et al. | 435/68.1 |
| 2007/0072214 A1* | 3/2007 | Garvin et al. | 435/6 |
| 2008/0166695 A1* | 7/2008 | Arduino et al. | 435/1.2 |

FOREIGN PATENT DOCUMENTS

| | | |
|---|---|---|
| JP | 05-076381 A | 3/1993 |
| JP | 11-056363 A | 3/1999 |
| JP | 2003-116590 A | 4/2003 |
| JP | 2004-141105 A | 5/2004 |
| JP | 2005-160446 A | 6/2005 |
| JP | 2006-061080 A | 3/2006 |
| JP | 2006-508672 A | 3/2006 |
| JP | 2008-514240 A | 5/2008 |
| WO | 02/102149 A1 | 12/2002 |
| WO | WO 2004/053053 A2 | 6/2004 |
| WO | WO 2006/039622 A2 | 4/2006 |

OTHER PUBLICATIONS

Brigotti, Maurizio, et al., "Effects of osmolarity, ions and compatible osmolytes on cell-free protein synthesis," Journal of Biochemical Society, 2003, pp. 369-374, vol. 369.
Zawada et al., "Effects of Growth Rate on Cell Extract Performance in Cell-Free Protein Synthesis", Wiley InterScience, 2006, p. 1-8.
Zawada et al., "Maintaining Rapid Growth in Moderate-Density *Escherichia coli* Fermentations", Wiley InterScience, 2005, p. 1-10.
Sitaraman et al., "High-Throughout Protein Expression Using Cell-Free System" cited in *Methods in Molecular Biology: High Throughput Protein Expression and Purification* by Doyle, 2009, 498:229-244.

* cited by examiner

*Primary Examiner* — Paul Zarek (74) *Attorney, Agent, or Firm* — Sughrue Mion, PLLC (57) ABSTRACT

This invention enables synthesis of proteins that were difficult to synthesize via a conventional cell-free protein synthesis system and increases the amount of proteins synthesized. Cell-free protein synthesis is carried out in a solution for cell-free protein synthesis containing a certain compound, such as trimethylglycine, L-carnitine, or sarcosine.

1 Claim, 7 Drawing Sheets

SOLUTION FOR CELL-FREE PROTEIN SYNTHESIS, KIT FOR CELL-FREE PROTEIN SYNTHESIS, AND METHOD OF PROTEIN SYNTHESIS

CROSS REFERENCE TO RELATED APPLICATION

This application is a National Stage of International Application No. PCT/JP2010/060112, filed on Jun. 15, 2010, claiming priority based on Japanese Patent Application No. 2009-142368, filed Jun. 15, 2009, the contents of all which are incorporated herein by reference in their entirety.

TECHNICAL FIELD

The present invention relates to a solution for cell-free protein synthesis, a kit for cell-free protein synthesis, and a method of protein synthesis in which a protein of interest is synthesized in a cell-free system (in vitro), which may be referred to as an in vitro protein synthesis system.

BACKGROUND ART

Up to the present, a cell-free protein synthesis system (i.e., an in vitro protein synthesis system) has been known as a technique of protein synthesis. Alternatively, a protein synthesis system comprising introducing a gene encoding a protein of interest into a live cell and separating and purifying the protein synthesized in a cell or culture solution is also known. In the case of the latter protein synthesis system, disadvantageously, it has been impossible to synthesize a protein that inhibits the growth of a cell to be used. In a cell-free protein synthesis system, however, a protein that is toxic to live cells can be synthesized.

In the cell-free protein synthesis system, however, it is known that some types of proteins are difficult to synthesize or cannot be synthesized in sufficient amounts. JP Patent Publication (kokai) No. H05-076381 (1993) A discloses a method for maintaining an energy source in order to accelerate a cell-free protein synthesis reaction, although such method is not always effective for proteins that are difficult to synthesize. As a method for synthesizing proteins that are difficult to synthesize, JP Patent Publication (kohyo) No. 2006-508672 A discloses a technique for modifying a DNA (mRNA) sequence. Such technique, however, lacks versatility since it must be exclusively designed for a relevant protein. JP Patent Publication (kokai) No. H11-056363 (1999) A discloses a technique in which large quantities of template DNA are contained in a reaction system so as to increase the amount of proteins synthesized. Such technique, however, would not enable the synthesis of proteins that are difficult to synthesize, and the effects of increasing the amount of proteins synthesized are not satisfactory.

SUMMARY OF THE INVENTION

Object to Be Attained by the Invention

As described above, no technique of synthesizing a sufficient amount of proteins in a cell-free protein synthesis system has previously been known. Under such circumstances, it is an object of the present invention to provide a solution for cell-free protein synthesis, a kit for cell-free protein synthesis, and a method of protein synthesis that can increase the amount of proteins synthesized in cases in which conventional cell-free protein synthesis systems yield small amounts.

Means for Attaining the Object

The present inventors have conducted concentrated studies in order to attain the above object. As a result, they discovered a group of compounds that can significantly increase the amount of proteins synthesized. This has led to the completion of the present invention.

Specifically, the solution for cell-free protein synthesis of the present invention comprises at least one compound selected from among the compounds represented by structural formulae (I) to (V). The solution for cell-free protein synthesis of the present invention may have a constitution similar to that of a known solution for cell-free protein synthesis, except that the solution of the present invention comprises the compound mentioned above. The solution for cell-free protein synthesis of the present invention is composed of at least one compound selected from among the compounds represented by structural formulae (I) to (V), and it is distinguished from solutions that have heretofore been referred to as "cell-free protein synthesis systems."

The kit for cell-free protein synthesis of the present invention comprises a solution for cell-free protein synthesis having the ability of protein synthesis and comprising at least one compound selected from among the compounds represented by structural formulae (I) to (V).

Regarding the kit for cell-free protein synthesis of the present invention, such compound may be mixed with a solution for cell-free protein synthesis in advance. The kit for cell-free protein synthesis of the present invention may comprise the solution containing the compound separately from the solution for cell-free protein synthesis.

Regarding the solution for cell-free protein synthesis and the kit for cell-free protein synthesis of the present invention, the compound may be at least one compound selected from the group consisting of carnitine, sarcosine, and trimethylglycine.

In addition, the kit for cell-free protein synthesis of the present invention may further comprise an expression vector capable of introducing a gene encoding a protein to be synthesized.

According to the method of protein synthesis of the present invention, protein synthesis is carried out in a solution for cell-free protein synthesis comprising at least one compound selected from among the compounds represented by structural formulae (I) to (V) and having the ability of protein synthesis.

The solution for cell-free protein synthesis of the present invention comprises at least one compound selected from among the compounds represented by structural formulae (I) to (V).

This description contains part or all of the contents as disclosed in the description and/or drawings of Japanese Patent Application No. 2009-142368, based on which the present application claims priority.

Effects of the Invention

The present invention can provide a solution for cell-free protein synthesis, a kit for cell-free protein synthesis, and a method of protein synthesis, which allows synthesis of proteins that were difficult to synthesize via conventional cell-free protein synthesis systems and can increase the amount of proteins synthesized. With the use of the solution for cell-free protein synthesis, the kit for cell-free protein synthesis, and the method of protein synthesis of the present invention, a wide variety of proteins can be synthesized in large quantities without complicated operations.

EMBODIMENTS FOR CARRYING OUT THE INVENTION

Hereafter, the present invention is described in detail.
Compounds Represented by Formulae (I) to (V)

The solution for cell-free protein synthesis of the present invention comprises at least one compound selected from among the compounds represented by structural formulae (I) to (V). Also, the kit for cell-free protein synthesis of the present invention comprises a solution for cell-free protein synthesis having the ability of protein synthesis and comprising at least one compound selected from among the compounds represented by structural formulae (I) to (V).

In structural formulae (I) to (V), $R^1$ to $R^3$ each independently represent a $C_{1-4}$, preferably $C_{1-2}$, and more preferably $C_1$ alkyl group. It is particularly preferable that at least one of $R^1$ to $R^3$ be a methyl group. In structural formulae (III) and (V), $R^4$ represents a side chain of an amino acid (excluding hydrogen). It is particularly preferable that $R^4$ represent a side chain of glycine, serine, threonine, asparagine, or glutamine because of neutral and hydrophilic properties of such amino acid side chain.

The value "n" in structural formulae (I) and (IV) and the sum of $n^1$ and $n^2$ in structural formula (II) are each 1 to 4, preferably 1 or 2, and more preferably 1. If the value "n" and the sum of $n^1$ and $n^2$ exceed the upper limit mentioned above, it disadvantageously becomes difficult to dissolve a compound in the solution for cell-free protein synthesis.

The compounds represented by structural formulae (I) to (V) are present in a solution for cell-free protein synthesis containing mRNA or cDNA encoding a protein to be synthesized. This advantageously enables synthesis of proteins that were difficult to synthesize by conventional techniques and increases the amount of proteins synthesized.

An example of the compound represented by structural formula (I) is trimethylglycine. Use of trimethylglycine as the compound represented by structural formula (I) is particularly preferable.

An example of the compound represented by structural formula (II) is L-carnitine. Use of L-carnitine as the compound represented by structural formula (II) is particularly preferable.

Examples of compounds represented by structural formula (III) include trimethyl serine, trimethyl asparagine, trimethyl threonine, and trimethyl glutamine.

An example of the compound represented by structural formula (IV) is sarcosine. Use of sarcosine as the compound represented by structural formula (IV) is particularly preferable.

The compounds represented by structural formulae (I) to (V) may be used alone or in combinations of two or more. Use of L-carnitine as the compound represented by any of structural formulae (I) to (V) is particularly preferable. When L-carnitine is used, the amount of proteins synthesized can be increased at a particularly significant level.

Trimethylglycine contained in the compounds represented by structural formulae (I) to (V) is known to resolve problems in annealing or extension reaction and to prevent inaccurate amplification when it is added to a reaction system at the time of amplification of a GC-rich domain via PCR (a DNA polymerase reaction), as described in U.S. Pat. No. 5,545,539. The compounds represented by structural formulae (I) to (V), however, can contribute to protein synthesis in a cell-free protein synthesis system, which is unrelated to the DNA polymerase reaction. When protein synthesis is carried out by adding mRNA encoding a protein to be synthesized to a solution for protein synthesis (i.e., a system that does not perform transcription), in particular, synthesis of proteins that were difficult to synthesize can be realized, and the amount of proteins synthesized can be increased.

The concentration of the compounds represented by structural formulae (I) to (V) in the solution for cell-free protein synthesis described below is not particularly limited. For example, it can be 10 to 3,000 mM, preferably 100 to 2,000 mM, and more preferably 200 to 1,000 mM. When the concentration of the compounds represented by structural formulae (I) to (V) is lower than the lower limit, disadvantageously, synthesis of proteins that were difficult to synthesize may become difficult, or the amount of proteins synthesized may not be increased. When the concentration of the compounds represented by structural formulae (I) to (V) is higher than the upper limit, disadvantageously, reactivity may be deteriorated due to the inhibitory action on enzymes related to protein synthesis, or operability may be deteriorated due to the increased viscosity of the solution.

Solution for Cell-Free Protein Synthesis

The term "solution for cell-free protein synthesis" refers to a solution that enables synthesis of a target protein by adding mRNA or DNA of a gene encoding such protein. In the present invention, a solution for cell-free protein synthesis is not particularly limited, and any solution that has been heretofore referred to as a cell-free protein synthesis system can be used. In general, a solution prepared by adding nucleic acids, amino acids, energy source, ions, buffer, or other additives to an extract of plants, bacteria, animal cells, or insect cells is used for a cell-free protein synthesis system. In particular, an extract of plant tissue or cells, bacteria, animal cells, or insect cells comprising a protein synthesis mechanism (e.g., ribosome) is used. In other words, the term "solution for cell-free protein synthesis" refers to a solution containing an extract that enables synthesis of a target protein by adding mRNA or DNA of a gene encoding such protein.

A solution for cell-free protein synthesis prepared by a conventional technique or a solution for cell-free protein synthesis included in a commercially available kit for cell-free protein synthesis may be used.

When preparing a solution for cell-free protein synthesis, for example, such extract should be first prepared. An extract is obtained by isolating cells typified by $E.$ $coli$, plant seed embryos, rabbit reticulocytes, or insect-derived cells and destroying such isolated cells via conventional techniques. Thereafter, insoluble substances are removed via centrifugation or other means. Endogenous DNA and RNA are degraded by a conventional technique, and endogenous amino acids, nucleic acids, nucleosides, or the like are removed or a pH level and a salt concentration is adjusted via dialysis of other means, according to need. The obtained extract retains the ability of protein synthesis including ribosome. When $E.$ $coli$ cells are used, the obtained extract may be occasionally referred to as an S30 extract.

Specifically, an $E.$ $coli$ extract can be prepared in accordance with the method described in, for example, Pratt, J. M. et al., Transcription and Translation, Hames, 179-209, B. D. & Higgins, S. J., eds., IRL Press, Oxford, 1984. A wheat germ extract can be prepared in accordance with the method described in, for example, Johnston, F. B. et al., Nature, 179, 160-161, 1957 or Erickson, A. H. et al., 1996, Meth. in Enzymol., 96, 38-50. Methods for preparing an extract from cells are not limited to those described above, and any methods can be employed.

After an extract is prepared as described above, ingredients necessary for protein synthesis can be added in order to prepare a solution for cell-free protein synthesis. Ingredients necessary for protein synthesis may be stored separately from the extract, and such ingredients may be mixed with the extract at the time of use. Ingredients necessary for protein synthesis are not particularly limited. Examples thereof include Tris-acetic acid, DTT, NTPs (ATP, CTP, GTP, and UTP), RNA polymerase, phosphoenolpyruvic acid, pyruvate kinase, at least one type of amino acid (including 20 types of naturally-occurring amino acids and derivatives thereof), polyethylene glycol (PEG), folic acid, cAMP, tRNA, ammonium acetate, potassium acetate, potassium glutamate, and magnesium acetate at the optimal concentration. When a protein is synthesized from mRNA separately prepared, it should be noted that NTPs (ATP, CTP, GTP, and UTP) or RNA polymerase serving as mRNA starting materials are not necessary. Antiseptics or other ingredients may be contained as the ingredients necessary for protein synthesis, in addition to the ingredients listed above.

A solution for cell-free protein synthesis contained in a commercially available kit for cell-free protein synthesis may be used. Examples of commercially available kits for cell-free protein synthesis include the TNT T7 Insect Cell Extract Protein Expression System, the TNT Coupled Reticulocyte Lysate Systems, the TnT Coupled Wheat GermExtract Systems, the $E.$ $coli$ T7 S30 Extract System for Circular DNA, the $E.$ $coli$ S30 Extract System for Circular DNA, and the $E.$ $coli$ S30 Extract Sysytem for Linear Templates available from Promega. An example of a commercially available solution for cell-free protein synthesis is the RTS 500 Rapid Translation System available from Roche.

Solution for Cell-Free Protein Synthesis, Kit for Cell-Free Protein Synthesis, and Method of Protein Synthesis The solution for cell-free protein synthesis of the present invention can have a composition similar to that of the a solution for cell-free protein synthesis described above, except that it comprises at least one compound selected from among the compounds represented by structural formulae (I) to (V). Since the solution for cell-free protein synthesis of the present invention comprises at least one compound selected from among the compounds represented by structural formulae (I) to (V), it can synthesize proteins that were difficult to synthesize with the use of the conventional solution for cell-free protein synthesis described above.

The kit for cell-free protein synthesis of the present invention comprises the solution for cell-free protein synthesis described above and at least one compound selected from among the compounds represented by structural formulae (I)

to (V). In the kit for cell-free protein synthesis, the compound may be added to the solution, which has been referred to as a cell-free protein synthesis system (i.e., a solution for cell-free protein synthesis), in advance (as defined as the solution for cell-free protein synthesis of the present invention above), or such compound may be separately prepared, so that it is added to the solution for cell-free protein synthesis at the time of use. Specifically, the kit for cell-free protein synthesis of the present invention is composed of at least one solution containing a compound represented by any of structural formulae (I) to (V), and it is provided in the form of a commercial product.

In the kit for cell-free protein synthesis, the solution for cell-free protein synthesis may be in the form of a solution prepared by mixing the extract with the ingredients necessary for protein synthesis in advance. Alternatively, the ingredients necessary for protein synthesis may be prepared separately, so that is is mixed with the extract at the time of use. According to an embodiment of the kit for cell-free protein synthesis of the present invention, specifically, the extract, the ingredients necessary for protein synthesis, and at least one compound selected from among the compounds represented by structural formulae (I) to (V) may be separately provided.

Any proteins can be synthesized without limitation. It is particularly preferable that targets of synthesis be proteins that were difficult to synthesize via conventional cell-free protein synthesis systems. Since a secondary structure, such as a stem-loop structure, is formed, for example, proteins that could not be synthesized via conventional cell-free protein synthesis systems can be the targets of synthesis.

The kit for cell-free protein synthesis of the present invention may add a gene encoding a protein to be synthesized in the form of DNA or mRNA.

When such gene is added in the form of DNA, it is necessary for the solution for cell-free protein synthesis to retain the ability of transcription; i.e., the mechanism of synthesizing mRNA from DNA, as well as the ability of translation. When such gene is added in the form of mRNA, the ability of transcription is not necessary, and retention of the ability of translation is sufficient.

The kit for cell-free protein synthesis of the present invention may comprise an expression vector used for incorporating DNA encoding a protein to be synthesized. It is preferable that an expression vector functions in a cell from which a solution for cell-free protein synthesis is derived. When a solution for cell-free protein synthesis is prepared from $E.$ $coli$ cells, specifically, any expression vector that is known to function in $E.$ $coli$ cells can be used. The same applies to the cases in which plant, animal, or insect cells are used.

When synthesizing target proteins with the use of the kit for cell-free protein synthesis of the present invention, at least one compound selected from among the compounds represented by structural formulae (I) to (V) described above mixed with a solution for cell-free protein synthesis and DNA and/or mRNA encoding such protein are mixed, and the resulting mixture is incubated at generally about 10° C. to 40° C. and preferably about 30° C. to 37° C., although the temperature is not particulaly limited thereto. The duration of synthesis via incubation is not particularly limited, and it is generally for about 30 minutes to 24 hours. Incubation may be carried out with agitation or shaking.

With the use of the kit for cell-free protein synthesis of the present invention, proteins that could not be synthesized via conventional cell-free protein synthesis systems can be synthesized. In addition, larger quantities of proteins can be synthesized, compared with the case in which conventional cell-free protein synthesis systems were employed.

EXAMPLES

Hereafter, the present invention is described in greater detail with reference to the examples, although the technical scope of the present invention is not limited to the following examples.

Example 1

In this example, the effects of a certain compound for accelerating protein synthesis were examined when the formic acid dehydrogenase gene derived from a $Gibberella$ mold ($Gibberella$ $zeae$) was expressed in a cell-free protein synthesis system.

(1) Reagent

A reagent manufactured by Nacalai Tesque, Inc. was used, unless otherwise specified.

Potassium phosphate buffer (KPB) (pH 7.5)
     <Solution A>0.5 M $KH_2PO_4$ 13.6 g/200 ml
     <Solution B>0.5 M $K_2HPO_4$ 26.13 g/300 ml
   0.5 M KPB (pH 7.5) was mixed with 16 ml of Solution A and 84 ml of Solution B.

Expressway Plus expression system (Invitrogen)
   1.62 M sodium formate (Na formate)
   5.5 g/50 ml 0.5 M KPB (pH 7.5)
   16.2 mM NAD
   It was dissolved in 0.5 M KPB (pH 7.5) to a concentration of 581 mg/50 ml.
   mPMS (DOJINDO) methoxy PMS 0.5 mg/ml
   WST1 (DOJINDO) 8 mg/ml
   PD medium
   Potato dextrose broth (Difco) (24 g/l). A pH level thereof was adjusted to 7, and it was autoclaved and used.
   100 mM $MgCl_2$
   $MgCl_2 \cdot 6H_2O$ 2.03 g/100 ml. It was autoclaved and used.
   KOD-Plus-: KOD-Plus-Polymerase (1 U/µl) (Toyobo Co., Ltd.)
   25 mM $MgSO_4$, 2 mM dNTP, 10×buffer
   Pfx Platinum Polymerase (2.5 U/µl) (Invitrogen)
   10×buffer, 10×enhancer, 2.5 mM dNTP, 50 mM $MgSO_4$
   Pyrobest DNA polymerase (Takara Bio Inc.)
   Triton X-100
   100 mM dATP, dCTP, dGTP, dTTP (Takara Bio Inc.)
   RNeasy Plant Mini Kit (QIAGEN)
   RNA PCR Kit (Takara Bio Inc.)
   MinElute Gel Extraction Kit (QIAGEN)
   MinElute PCR Purification Kit (QIAGEN)
   $dH_2O$: DNase/RNase Free Distilled Water (Invitrogen)
   Restriction enzymes NdeI/EcoRI (Takara Bio Inc.)
   DNA Ligation kit ver 2.1, solution I (Takara Bio Inc.)
   JM109 Competent Cells (Takara Bio Inc.)
   pET-23b (+) vector (Novagen)
   pT7 Blue T-vector (Novagen)
   $E.$ $coli$ One Shot BL21 (Star) competent cells (Invitrogen)
   Chaperone expression plasmid
   TaKaRa Chaperone Plasmid Set (TaKaRa)
   Plasmid pG-KJE8
   Chaperone dnaK-dnaJ-grpE-groES-groEL
   Glass beads for fragmentation, YGBLA-01 (low alkaline (0.1)) (Yasui Kikai Corporation)
   Dialysis membrane (Sanko Junyaku Co., Ltd.), dialysis membrane size: 18/32
   Transcend tRNA (Promega)
   Transcend Non-Reactiove Translation Detection System (Promega)
   25% (W/V) glucose (Wako)
   34 mg/ml chloramphenicol (dissolved in ethanol)

15 mg/ml thiamine (Wako)
1 M IPTG
5 µg/ml tetracycline
2.2 mM Tris-acetate (pH 8.2) (SIGMA) was sterilized and used.
1 M magnesium acetate (pH 7.0)
3.6 M potassium acetate (pH 7.0)
1 M DTT (Wako)
50 µg/ml PMSF (in ethanol)
50 mM NTPs (equivalent amounts of 200 mM ATP, CTP, GTP, and CTP were mixed).
200 mM ATP (Yamasa Corporation)
200 mM CTP (Roche)
200 mM UTP (Roche)
200 mM GTP
1 M Hepes-KOH (pH 7.5)
3 M potassium glutamate
2 M ammonium acetate
20 mg/ml E. coli tRNA (Roche)
1 mg/ml rifampicin (Wako)
5 M creatine phosphate (Wako)
12 mg/ml creatine kinase (Wako)
12.12 g/1.01 ml (165 units/mg, 2,000 units were used)
Amino acid mix (total amount: 1 ml, composed as indicated below)
RPM1 1640 50× (SIGMA) 800 µl
50 mM glutamine (Kyowa Hakko Kogyo Co., Ltd.) 100 µl
50 mM alanine (Kyowa Hakko Kogyo Co., Ltd.) 100 µl
5.7 M betain (trimethylglycine) (Fluka)
60% PEG6000 (W/V)
LB (Cm) plate (total amount: 200 ml, composed as indicated below)
LB Broth, Lennox (Difco) 4 g
34 mg/ml chloramphenicol 117.6 µl
Agar, Powder (Wako) 3 g
$dH_2O$ 200 ml
After sterilized in an autoclave, chloramphenicol was added, and the mixture was fractionated to a dish.
LB (Cm) liquid medium (total amount: 48.3 ml, composed as indicated below)
LB liquid medium (LB Broth (Difco) 20 g/l) 48 ml
34 mg/ml chloramphenicol 28.16 µl
Growth medium (for main culture) (total amount: 1 l, composed as indicated below)
$KH_2PO_4$ 5.6 g
$K_2HPO_4$ $_b$ 28.9g
Yeast extract (Difco) 10 g
$dH_2O$ (added to bring the amount of the solution to 1 liter)
20 µg/ml chloramphenicol
25% (WN) glucose (24 ml) and 15 mg/ml thiamine (600 µl) were added to 600 ml of the medium.
Wash buffer
10 mM Tris-acetate (pH 8.2)
12 mM magnesium acetate (pH 7.0)
60 mM KCl
1 mM DTT
50 µg/ml PMSF
Lysis buffer
10 mM Tris-acetate (pH 8.2)
12 mM magnesium acetate (pH 7.0)
60 mM potassium acetate (pH 7.0)
1 mM DTT
Preincubation buffer
1.2M Tris-acetate (pH 8.2)
47 mM magnesium acetate (pH 7.0)
15 mM DTT
Amino acid mix
12 mM ATP
100 mM creatine phosphate
0.4 mg/ml creatine kinase
Dialysis buffer
10 mM Tris-acetate (pH 8.2)
12 mM magnesium acetate (pH 7.0)
60 mM potassium acetate (pH 7.0)
1 mM DTT
50 µg/ml PMSF (2) Cloning of *Gibberella zeae* FDH Gene (2-1) Microbial Strain The *Gibberella zeae* strain (NBRC No. 4474) was purchased from the NITE Biological Resource Center (hereafter referred to as "NBRC"), which is an affiliated organization of the National Institute of Technology and Evaluation, renatured by a designated method, and cultured using a PD (potato dextrose) medium.

(2-2) Isolation of Formic Acid Dehydrogenase Gene (2-2-1) Amplification of Formic Acid Dehydrogenase Gene Total RNA (including mRNA, rRNA, and tRNA) was prepared from the strain obtained via culture in the method described in 2-1 using the RNeasy Plant Mini Kit (QIAGEN). At the outset, cDNA was synthesized from a total RNA template using the RNA PCR Kit (Takara Bio Inc.). Table 1 shows a composition of the reaction solution.

TABLE 1

| (Composition of reaction solution) Final concentration |
| --- |
| 5 mM $MgCl_2$ |
| 1× RT buffer |
| 1 mM dNTP mixture |
| 0.5 U RNase Inhibitor |
| 0.25 U AMV Reverse Transcriptase XL |
| 0.125 µM Oligo dT-Adpoter primer |
| 5 µg Total RNA |

RNase free $H_2O$ was added to bring the amount of the solution to 10 µl.

A cDNA synthesis reaction was carried out through a reaction cycle of 50° C. for 2 hours, 99° C. for 5 minutes, and 4° C. with the use of a reaction solution having the composition above.

Subsequently, PCR was carried out using the synthesized cDNA as a template and Pyrobest DNA polymerase. Table 2 shows the ingredients of 50 µl of the reaction solution.

TABLE 2

| (Composition of reaction solution) |
| --- |
| 1× Pyrobest buffer |
| 200 µM dNTPs mixture |
| 2.5 U Pyrobest DNA polymerase |
| 50 pmol Primer (forward) |
| 50 pmol Primer (reverse) |
| 10 µl cDNA solution |

Sterilized water was added to bring the amount of the solution to 50 µl.

With the use of the reaction solution having the composition above, PCR was carried out through 25 cycles of 95° C. for 1 minute, 95° C. for 30 seconds, 60° C. for 30 seconds, and 72° C. for 1 minute, followed by a cycle of 72° C. for 10 minutes and 4° C. This PCR operation involved the use of a pair of primers Gib FDH1-F-NdeI (forward): CGC CAT ATG GTC AAG GTT CTT GCA GTT C (SEQ ID NO: 1) and Gib FDH1-R (reverse): CTA TTT CTT CTC ACG CTG ACC (SEQ ID NO:2).

(2-2-2) Cloning and Structural Analysis of Formic Acid Dehydrogenase Gene

Figure 1:
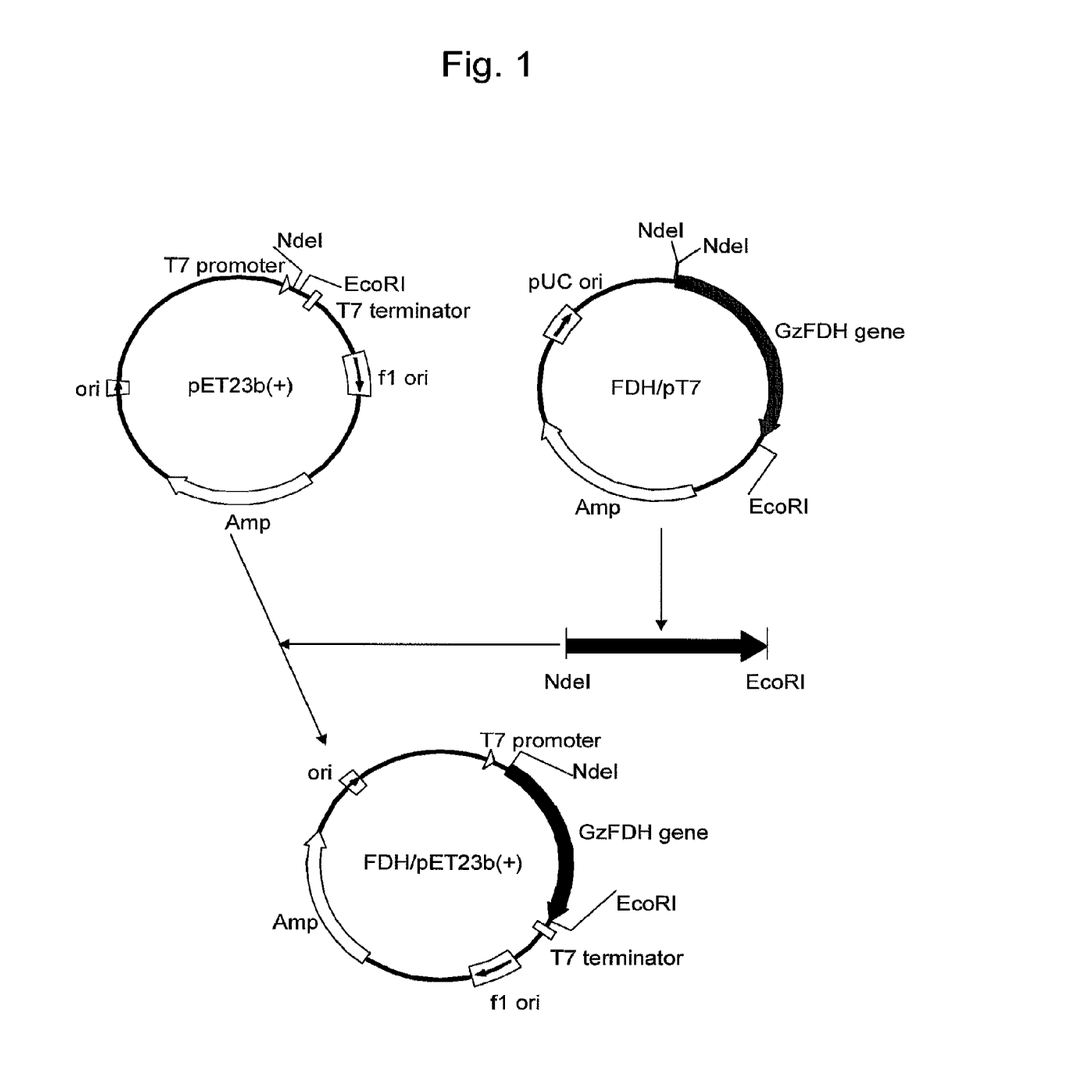
FIG. 1 is a schematic diagram showing a process for constructing G. zeae-derived FDH(GzFDH)/pET23b(+).

After the sizes of various PCR products were confirmed via agarose gel electrophoresis, the PCR products purified from agarose gel with the use of the MinElute Gel Extraction Kit (QIAGEN) were subcloned using the pT7 Blue T-vector (Novagen) and the JM109 competent cells (Takara Bio Inc.) (GzFDH/pT7) (see FIG. 1). The sequence of the isolated formic acid dehydrogenase gene (SEQ ID NO: 3) exhibited 100% identity with the sequence stored in the database open to public (Genbank No. XP_386303) at the amino acid level. SEQ ID NO: 4 shows the amino acid sequence of formic acid dehydrogenase encoded by the isolated formic acid dehydrogenase gene.

(2-2-3) Preparation of Formic Acid Dehydrogenase Gene Expression Vector

The FDH/pT7 plasmid prepared in 2-2-2 was treated with the NdeI/EcoRI restriction enzymes. Table 3 shows a composition of the reaction solution. Treatment with restriciton enzymes was carried out at 37° C. for 2 hours.

TABLE 3

(Composition of reaction solution)
Final concentration

| 1x Universal buffer H |
| 25 U NdeI |
| 25 U EcoRI |
| 5 µg GzFDH/pT7 |

Sterilized water was added to bring the amount of the solution to 20 µl.

The solution after the reaction was subjected to 0.8% agarose gel electrophoresis, the formic acid dehydrogenase gene (about 1.1 kb) cleaved from the vector as the NdeI/EcoRI fragment was purified using the MinElute Gel Extraction Kit (QIAGEN). Subsequently, the formic acid dehydrogenase gene fragment was introduced into the NdeI/EcoRI site of the gene expression vector (pET23b (+), Novagen) treated with restriction enzymes in the same manner as in the case of FDH/pT7 using the DNA Ligation kit Ver.2.1 (Takara Bio Inc.) and then subcloned into JM109 competent cells (Takara Bio Inc.) (FDH/pET23b (+)) (see FIG. 1).

(3) Cell-Free Protein Synthesis
(3-1) Preparation of Template DNA

PCR was carried out under the conditions indicated below with the use of the *Gibberella*-derived FDH gene introduction vector obtained in (2) above as a template. Table 4 shows the ingredients of 50 µl of the reaction solution. This PCR operation involved the use of a pair of primers Single-F: CGATC-CCGCGAAATTAATACGACT (SEQ ID NO: 5) and Single-R1:TCCGGATATAGTTCCTCCTTTCAG (SEQ ID NO: 6).

TABLE 4

| 10x Buffer | 5 µl |
| dNTP (2 mM each) | 5 µl |
| MgSO4 (25 mM) | 2 µl |
| Single-F (10 pmol/µl) | 1.5 µl |
| Single-R1 (10 pmol/µl) | 1.5 µl |
| KOD-Plus-DNA Polymerase (1 U/µl) | 1 µl |
| Template plasmid DNA | 0.3 µl |
| dH2O | 33.7 µl |

With the use of the reaction solution having the composition above, PCR was carried out through 30 cycles of 94° C. for 2 minutes, 94° C. for 15 seconds, and 60° C. for 1 minute and 30 seconds, followed by a cycle of 68° C. for 2 minutes and 4° C. The amplified fragment (about 1.4 kbp) was purified using the MinElute PCR Purification Kit and used for translation.

(3-2) Preparation of Template mRNA

The *Gibberella*-derived FDH gene obtained in 3-1 above and a DNA fragment containing T7 promoter/terminater were used as templates, and transcription was carried out under the conditions indicated below. The transcription reaction involved the use of the MEGAscript kit (Ambion). Table 5 shows the ingredients of 20 µl of the reaction solution.

TABLE 5

| 10x reaction Buffer | 2 µl |
| ATP solution | 2 µl |
| UTP solution | 2 µl |
| GTP solution | 2 µl |
| CTP solution | 2 µl |
| Template DNA | 1 µl (1 µg) |
| Enzyme mix | 2 µl |
| dH2O | 7 µl |

The transcription reaction was carried out at 37° C. for 3 hours. Thereafter, 1 µl of TURBO DNase was added to the reaction solution and held at 37° C. for 15 minutes. Thereafter, 9 µl of dH2O and 30 µl of the lithium chloride precipitation solution were added thereto, and the mixture was held at −20° C. for 30 minutes. Thereafter, the resultant was centrifuged at 13,000×g for 15 minutes, and the supernatant was removed. The precipitate was rinsed with 70% ethanol and then dissolved in 20 µl of dH2O.

(3-3) Preparation of *E. coli* S30 Fraction
Preculture

The pG-KJE8 expression plasmids were introduced into the *E. coli* BL21 (DE3) star cells. Single colonies were formed from the transformed *E. coli* cells on an LB (Cm) plate and cultured in LB (Cm) liquid medium (a 150 ml/500 ml-flask), and glycerol stocks thereof were prepared, followed by storage at −80° C. Preculture was conducted at 37° C. overnight with shaking at 130 rpm after 88 µl of 34 mg/ml chloramphenicol was added.

Main Culture

The preculture solution (30 ml) was added to 600 ml of growth medium, and shake culture was carried out at 37° C. and 130 rpm for 3.5 hours (until A600 approximated 1.5). Thereafter, IPTG for T7 RNA polymerase induction was added (600 ml/2 liters per flask). Thereafter, 600 µl of 5 µg/ml tetracycline (final concentration: 5 ng/ml) and 600 µl of 500 mg/ml L-arabinose (final concentration: 500 µg/ml) were added as reagents for chaperone induction (600 ml/2 liters per flask). Shake culture was then carried out at 30° C. and 130 rpm for 1.5 hours (until A600 approximated 3 to 4).

Harvesting and Washing

After the completion of culture, the culture solution was transferred to a 250-ml centrifuge tube, and the supernatant was removed via centrifugation (7,000 rpm, 7 minutes, 4° C.) (BECKMAN JA-14). After the cells were suspended in 10 ml of wash buffer, the supernatant was removed via centrifugation (7,000 rpm, 7 minutes, 4° C.) (BECKMAN JA-14).

Disruption

Cells (10 g) were suspended in 9 ml of lysis buffer and transferred to a disruption tube (Yasui Kikai Corporation). Glass beads (19 g, Yasui Kikai Corporation) were added thereto, and the cells were subjected to disruption using the Multi-Beads Shocker (Yasui Kikai Corporation) (60 seconds on/off, 4 cycles).

Superdrawing (Preparation of S30)

The obtained solution of the disrupted cells was centrifuged (6,000 rpm, 10 minutes, 4° C.) (BECKMAN JA-12), and the supernatant was recovered. Further, the resultant was subjected to ultracentrifugation twice (i.e., centrifugation was carried out at 16,000 rpm (30,900 G) for 25 minutes at 4° C. and then at 17,000 rpm (34,957 G) for 35 minutes at 4° C.) (BECKMAN JA-20), and the supernatant was recovered.

Preincubation

Preincubation buffer was added in an amount 15% that of the supernatant obtained via ultracentrifugation (the S30 fraction), and the mixture was incubated at 28° C. for 1.5 hours.

Dialysis

A dialysis membrane used for preparing S30 fractions via dialysis was prepared in the following manner. At the outset, a dialysis membrane of about 15 cm was prepared relative to 10 ml of S30 fractions (the amount of the solution of S30 fractions (ml)+about 5 cm). The dialysis membrane soaked in $dH_2O$ was subjected to boiling in a microwave oven and agitated with the use of a stirrer (for 2 hours or longer). Thereafter, the membrane was introduced into a dialysis buffer and agitated with a stirrer (for 5 minutes or longer).

Dialysis was carried out in the following manner. At the outset, 500 ml of a dialysis buffer was introduced into a 1-liter plastic beaker, the S30 fractions were introduced therein to a height approximately 70% of the dialysis membrane, and the beaker was closed with the use of a clip exclusively intended for such use. Thereafter, the solution was agitated with a stirrer at 4° C. for 45 minutes (at a speed at which a dialysis membrane would slowly rotate). Thereafter, 500 ml of the dialysis buffer was exchanged with fresh buffer, and the product was recovered in a 50-ml corning tube. Thereafter, centrifugation was carried out at 6,900 rpm for 10 minutes at 4° C. (BECKMAN JA-12), the supernatant was recovered, and 1-ml-each fractions were stored at -80° C.

(3-4) Cell-Free Translation (3-4-1) Translation Via Expressway Plus Expression System (Invitrogen)

With the use of template DNA or template mRNA fragments prepared in 3-1 and 3-2 and the Expressway cell-free *E. coli* expression system, the translation reaction (the transcription/translation coupled reaction) was carried out. Table 6 shows the ingredients of 10 μl of the reaction solution. The reaction was carried out at 25° C. for 2 hours. The reaction was carried out with the use of the solution having the composition as shown in Table 6 and with the use of the solution prepared by adding 0.5 M trimethylglycine to the solution shown in Table 6.

TABLE 6

| IVPS Plus *E. coli* extract | 4 μl | |
|---|---|---|
| 2.5x IVPS plus *E. coli* reaction buffer | 4 μl | |
| T7 enzyme mix | 0.2 μl | |
| 75 mM methionine | 0.2 μl | |
| Template DNA | 1.6 μl | (500 ng) |

(3-4-2) Translation Using S30 Fractions

With the use of template DNA or template mRNA fragments prepared in 3-1 and 3-2 and the S30 fractions derived from *E. coli* prepared in 3-3, the translation reaction (or the transcription/translation coupled reaction) was carried out. Table 7 shows the ingredients of 11.12 μl of the reaction solution. The reaction was carried out at 25° C. for 1.5 hours.

TABLE 7

| S30 fraction | 5 μl |
|---|---|
| 50 mM NTP | 0.2 μl |
| 1M Hepes-KOH (pH 7.5) | 0.55 μl |
| 3M potassium glutamate | 0.7 μl |
| 2M ammonium acetate | 0.14 μl |
| 0.1M DTT | 0.14 μl |
| 20 mg/ml *E. coli* tRNA | 0.08 μl |
| 1 mg/ml rifampicin | 0.08 μl |
| 12 mg/ml creatine kinase | 0.08 μl |
| 5M creatine phosphate | 0.15 μl |
| Amino acid mix | 0.3 μl |
| 100 mM cAMP | 0.4 μl |
| Betaine | 1.2 μl |
| Mg(OAc)$_2$ | 0.5 μl |
| 60% PEG6000 (W/V) | 0.6 μl |
| Template DNA (equivalent to 300 ng) | 1.0 μl |

In the above reaction solution, the final concentration of betaine (trimethylglycine) was adjusted to 0.5 M at most, and that of Mg (OAc)$_2$ was adjusted to 10 mM. When an mRNA template is used for the reaction solution, the amount thereof was 1 μg.

Transcend tRNA (0.2 μl, Promega) was added to the reaction solution, and the translation reaction (or the transcription/translation coupled reaction) was carried out. The translation solution (2 μl) was subjected to SDS-PAGE (reduction), and the synthesized product was detected via blotting using the Transcend non-reactive translation detection system. The amount of synthesis was quantified using SigmaScanPro.

(4) Detection of Synthetic Protein

The expression level of the formic acid dehydrogenase gene was evaluated by assaying the formic acid dehydrogenase activity (FDH activity). The formic acid degradation reaction by FDH is represented by the following formula.

$$HCOO^- + NAD^+ \rightarrow CO_2 + NADH$$

With the addition of an electron carrier (i.e., Methoxy PMS (mPMS)) and an oxidation-reduction indicator (WST1) (both manufactured by DOJINDO), the reaction proceeds as represented by the formula below. By assaying yellow formazan at the absorbance of 438 nm, accordingly, the amount of formic acid degradation can be quantified. The absorbance coefficient of yellow formazan is approximately 6 times higher than that of NADH, and quantification can be carried out with higher sensitivity than direct assaying of NADH.

$$NADH + mPMS \rightarrow NAD^+ + mPMS \text{ (reducing)}$$

$$mPMS \text{ (reducing)} + WST1 \rightarrow mPMS + \text{yellow formazan}$$
$$(37,000/M \cdot cm, 438 \text{ nm})$$

By assaying the absorbance at 430 nm using a plate reader (Spectrafluor Plus TECAN), yellow formazan can be quantified, and FDH activity expressed via the cell-free protein synthesis system; i.e., the amount of FDH synthesized, can be evaluated.

(4-1) Assay of FDH Activity

FDH activity was assayed using the reaction solution having the composition shown in Table 8. The reaction was carried out via heating at 37° C. in a thermal cycler for about 30 minutes, and the tube was removed and placed on ice to terminate the reaction. Thereafter, the absorbance at 430 nm was assayed using a plate reader (Spectrafluor Plus: TECAN) to detect FDH activity.

TABLE 8

| 1.62M sodium formate | 10 μl |
|---|---|
| 16.2 mM NAD | 10 μl |
| 100 mM KPB (pH 7.5) | 74.63 μl |

TABLE 8-continued

| 0.5 mg/ml mPMS | 0.67 μl |
| 8 mg/ml WST1 | 2.7 μl |

Figure 2:
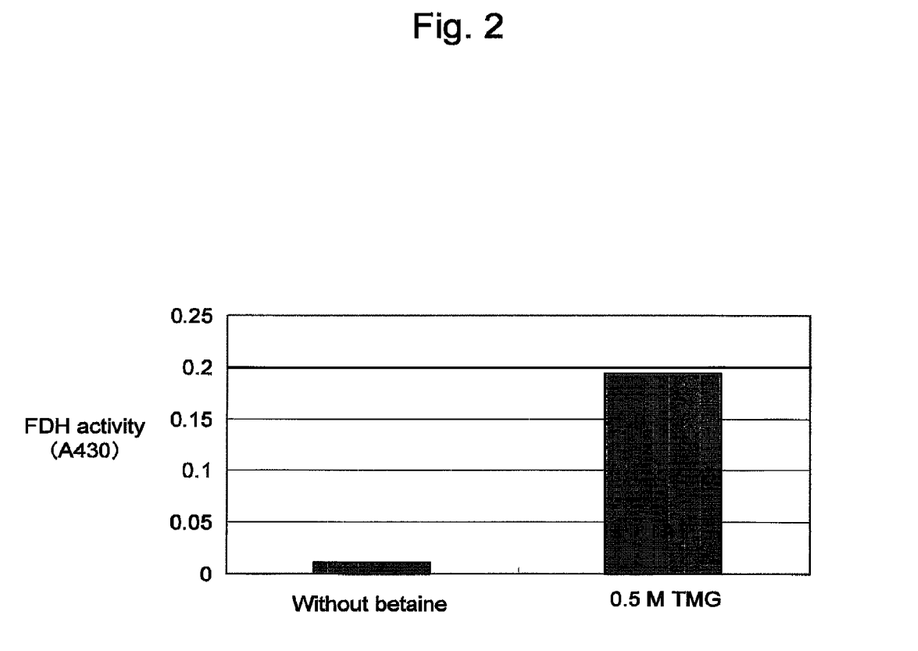
FIG. 2 is a characteristic diagram showing the results of measuring the FDH activity after FDH has been synthesized in a commercially available solution for cell-free protein synthesis in the presence or absence of betaine (trimethylglycine).

The results attained by the assay conducted in 3-4-1 with the use of template DNA prepared in 3-1 above are shown in FIG. 2. As shown in FIG. 2, FDH activity was significantly enhanced when cell-free protein synthesis was carried out in the presence of trimethylglycine, compared with FDH activity assayed in the absence of trimethylglycine, and the amount of proteins synthesized increased.

Figure 3:
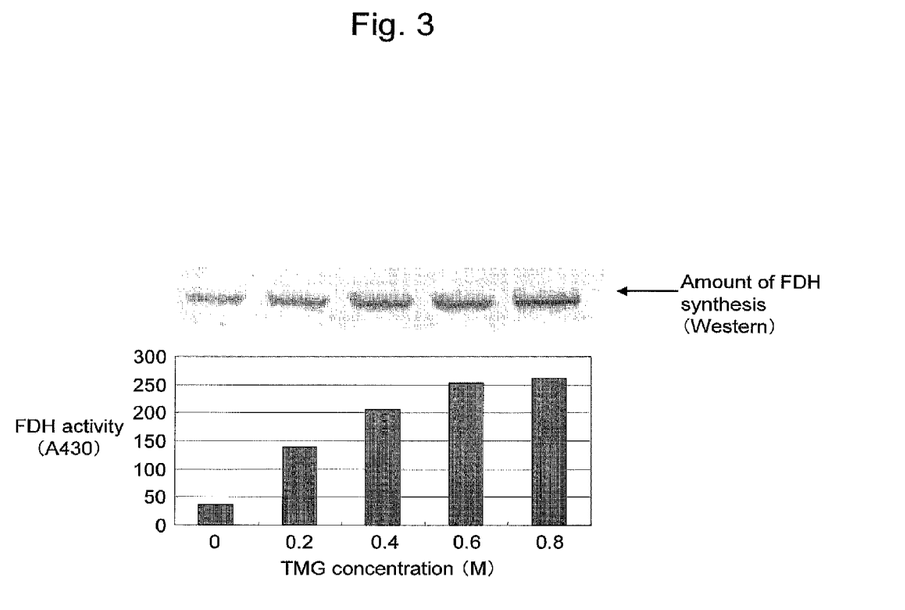
FIG. 3 is a characteristic diagram showing the results of measuring the FDH activity (the lower part) and the results of Western blotting (the upper part) after FDH has been synthesized from template cDNA in a reaction solution for cell-free protein synthesis using S30 fractions derived from E. coli in the presence or absence of betaine (trimethylglycine) at different concentrations.
Figure 4:
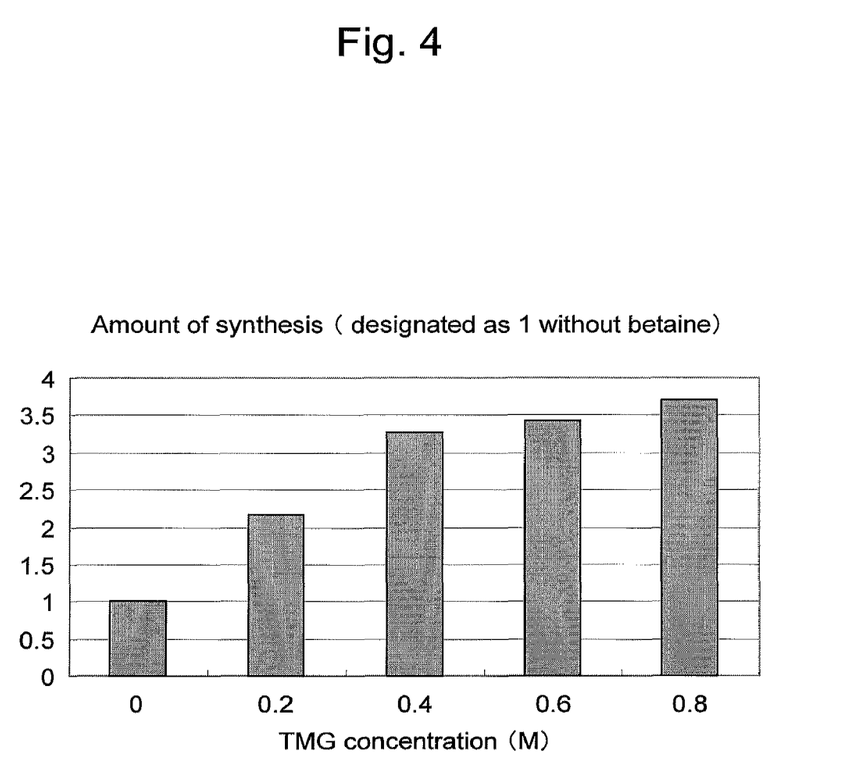
FIG. 4 is a characteristic diagram showing the results of quantification of FDH synthesis amount using the results of Western blotting shown in FIG. 3.

The results of SDS-PAGE conducted in 3-4-2 using template DNA prepared in 3-1 are shown in the upper portion of FIG. 3, and the results of FDH activity assay are shown in the lower part of FIG. 3. FIG. 4 shows the results of assay of the amount of proteins synthesized based on the results of SDS-PAGE. In FIG. 4, the amount of proteins synthesized is represented by a relative value based on the amount of synthesis 1, which is attained without the addition of trimethylglycine.

As shown in FIG. 3 and FIG. 4, FDH activity and the amount of FDH synthesis were significantly improved when cell-free protein synthesis was carried out in the presence of trimethylglycine, compared with the case in which such protein synthesis was carried out in the absence of trimethylglycine. In addition, FDH activity and the amount of FDH synthesis increased depending on the trimethylglycine concentration.

Figure 5:
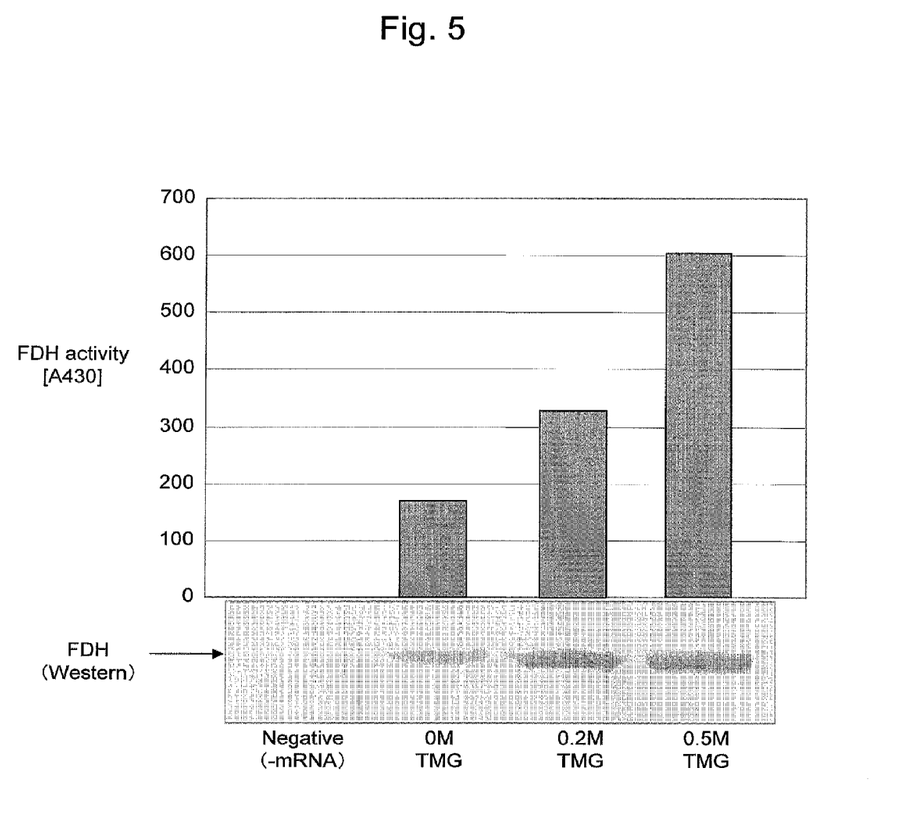
FIG. 5 is a characteristic diagram showing the results of measuring the FDH activity (the upper part) and the results of Western blotting (the lower part) after FDH has been synthesized from template mRNA using a kit for cell-free protein synthesis using S30 fractions derived from E. coli in the presence or absence of betaine (trimethylglycine) at different concentrations.
Figure 6:
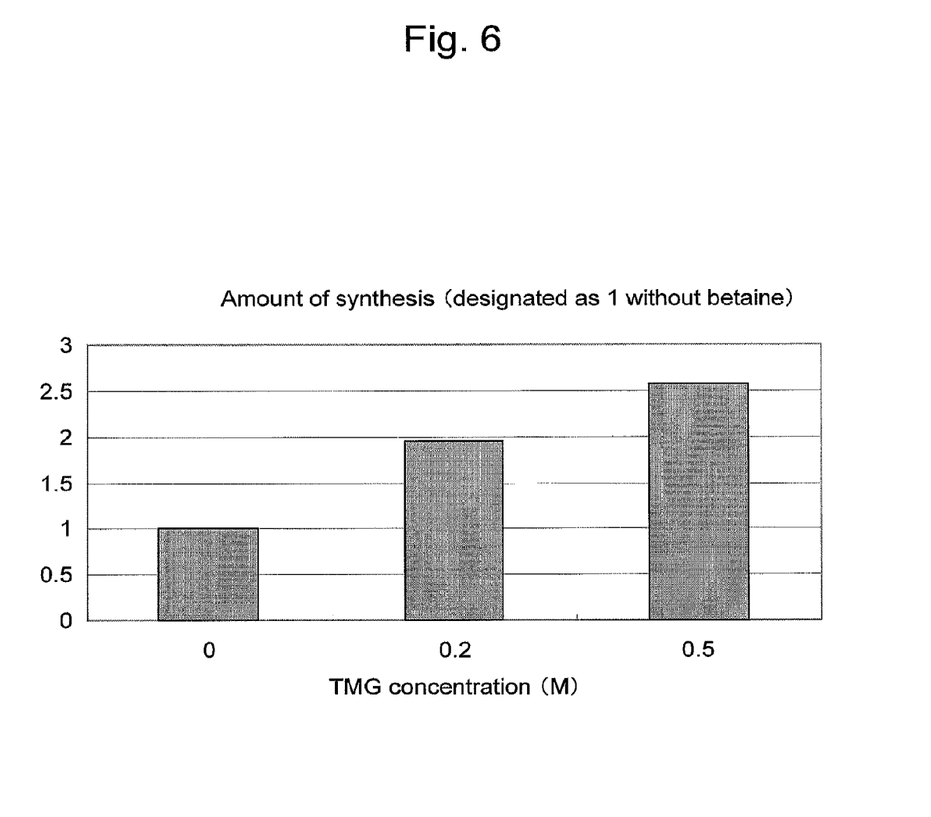
FIG. 6 is a characteristic diagram showing the results of quantification of FDH synthesis amount using the results of Western blotting shown in FIG. 5.

Further, the results of FDH activity assay conducted in 3-4-2 using template mRNA prepared in 3-2 are shown in the upper part of FIG. 5, and the results of SDS-PAGE are shown in the lower part of FIG. 5. Also, the results of assay of the amount of proteins synthesized based on the results of SDS-PAGE are shown in FIG. 6. In FIG. 6, the amount of proteins synthesized is represented by a relative value based on the amount of synthesis 1, which is attained without the addition of trimethylglycine.

As shown in FIG. 5 and FIG. 6, FDH activity and the amount of FDH synthesis were significantly improved when cell-free protein synthesis was carried out in the presence of trimethylglycine, compared with the case in which such protein synthesis was carried out in the absence of trimethylglycine. In addition, FDH activity and the amount of FDH synthesis increased depending on the trimethylglycine concentration.

The above results demonstrate that trimethylglycine exhibits the activity of improving translation efficiency for a gene encoding a target protein in a cell-free protein synthesis system.

Figure 7:
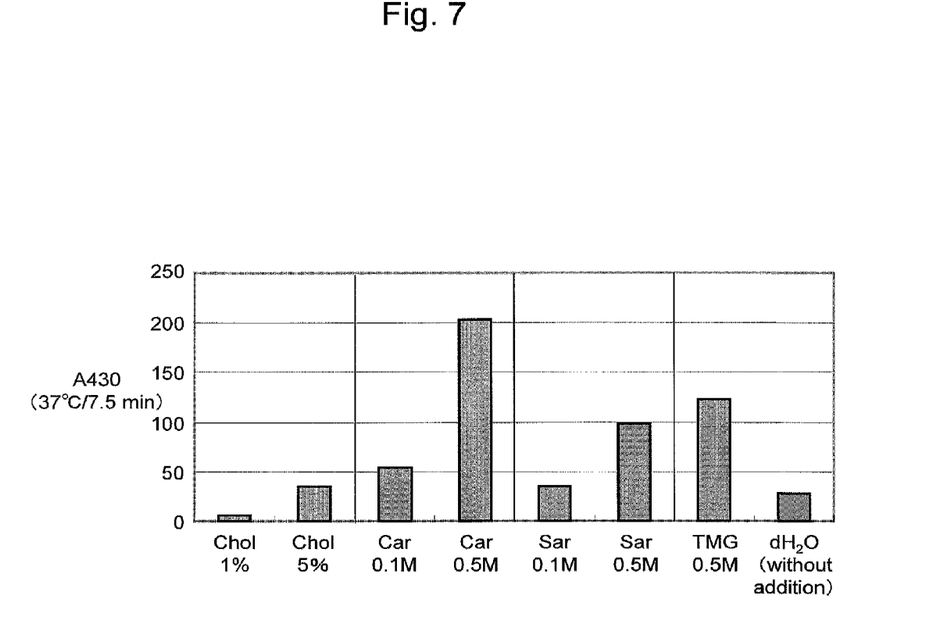
FIG. 7 is a characteristic diagram showing the results of comparison of the capacity of trimethylglycine, L-carnitine, sarcosine, and choline for accelerating protein synthesis.

Further, FIG. 7 shows the results of protein synthesis conducted with the use of L-carnitine (Car), sarcosine (Sar), and choline (Chol, $(CH_3)_3N^+CH_2CH_2OH$ Cl) instead of trimethylglycine in 3-4-2 conducted with the use of template mRNA prepared in 3-2. The results shown in FIG. 7 demonstrate that the ability of protein synthesis via a cell-free protein synthesis system can be enhanced in the presence of a compound selected from among L-carnitine, sarcosine, and choline. When L-carnitine is used, in particular, the ability of protein synthesis via a cell-free protein synthesis system is found to be remarkable. The results demonstrate that L-carnitine, sarcosine, and choline improve the translation efficiency for a gene encoding a target protein in a cell-free protein synthesis system, as with trimethylglycine.

All publications, patents, and patent applications cited herein are incorporated herein by reference in their entirety.

The invention claimed is:

1. A method of protein synthesis, which is carried out in a solution for cell-free protein synthesis comprising at least one compound selected from the group consisting of carnitine and sarcosine.

* * * * *

SEQUENCE LISTING

```
<160> NUMBER OF SEQ ID NOS: 6

<210> SEQ ID NO 1
<211> LENGTH: 28
<212> TYPE: DNA
<213> ORGANISM: Artificial
<220> FEATURE:
<223> OTHER INFORMATION: Synthesized DNA

<400> SEQUENCE: 1
cgccatatgg tcaaggttct tgcagttc                                         28

<210> SEQ ID NO 2
<211> LENGTH: 21
<212> TYPE: DNA
<213> ORGANISM: Artificial
<220> FEATURE:
<223> OTHER INFORMATION: Synthesized DNA

<400> SEQUENCE: 2
ctatttcttc tcacgctgac c                                               21

<210> SEQ ID NO 3
<211> LENGTH: 1098
<212> TYPE: DNA
<213> ORGANISM: Gibberella zeae
<220> FEATURE:
<221> NAME/KEY: CDS
<222> LOCATION: (1)..(1098)

<400> SEQUENCE: 3
```

-continued

```
atg gtc aag gtt ctt gca gtt ctc tac gac ggt ggc cag cac gcc aag    48
Met Val Lys Val Leu Ala Val Leu Tyr Asp Gly Gly Gln His Ala Lys
1               5                   10                  15 gat caa ccc ctc ctt ctc gga aca act gag aac gag ctc ggc atc cgc    96
Asp Gln Pro Leu Leu Leu Gly Thr Thr Glu Asn Glu Leu Gly Ile Arg
            20                  25                  30 aag tgg ctc gag gac caa ggt cac act ctt gtc acc act tcc gac aag   144
Lys Trp Leu Glu Asp Gln Gly His Thr Leu Val Thr Thr Ser Asp Lys
        35                  40                  45 gac cgt gag ggt tcc aaa ttc gac gag gag ctc gag gat gct gag att   192
Asp Arg Glu Gly Ser Lys Phe Asp Glu Glu Leu Glu Asp Ala Glu Ile
    50                  55                  60 atc atc acc act ccc ttc cac cct ggt tac ctg acc gct gag cgt ctg   240
Ile Ile Thr Thr Pro Phe His Pro Gly Tyr Leu Thr Ala Glu Arg Leu
65                  70                  75                  80 gcc aag gcc aag aag ctc aag ctc gct gtt acc gct ggt atc ggc tcc   288
Ala Lys Ala Lys Lys Leu Lys Leu Ala Val Thr Ala Gly Ile Gly Ser
                85                  90                  95 gac cac gtc gac ctc aac gct gcc aac aag acc aac ggc ggt atc acc   336
Asp His Val Asp Leu Asn Ala Ala Asn Lys Thr Asn Gly Gly Ile Thr
            100                 105                 110 gtt gct gag gtc act ggc tcc aac gtc gtc tct gtt gct gag cac gtt   384
Val Ala Glu Val Thr Gly Ser Asn Val Val Ser Val Ala Glu His Val
        115                 120                 125 ctc atg acc atc ctc gtc ctc atc cgc aac ttc gtc cct gcc cac gag   432
Leu Met Thr Ile Leu Val Leu Ile Arg Asn Phe Val Pro Ala His Glu
    130                 135                 140 cag atc gag gct ggt gag tgg gac gtc gcc cat gct gct aag cag gag   480
Gln Ile Glu Ala Gly Glu Trp Asp Val Ala His Ala Ala Lys Gln Glu
145                 150                 155                 160 ttc gac ctt gag ggc aag gtt gtc ggc act gtc gct gtc ggc cgc atc   528
Phe Asp Leu Glu Gly Lys Val Val Gly Thr Val Ala Val Gly Arg Ile
                165                 170                 175 ggt gag cgt gtc ctc cgc cgc ctc aag cct ttc gac tgc aag gag ctc   576
Gly Glu Arg Val Leu Arg Arg Leu Lys Pro Phe Asp Cys Lys Glu Leu
            180                 185                 190 ctc tac ttc gac tac cag ccc ctt tcc ccc gag gct gag aag gag atc   624
Leu Tyr Phe Asp Tyr Gln Pro Leu Ser Pro Glu Ala Glu Lys Glu Ile
        195                 200                 205 ggc tgc cgc cgc gtc gac act ctc gag gag atg ctc gct cag tgt gat   672
Gly Cys Arg Arg Val Asp Thr Leu Glu Glu Met Leu Ala Gln Cys Asp
    210                 215                 220 att gtc acc atc aac tgc cct ctc cac gag aag acc aag ggt atg ttc   720
Ile Val Thr Ile Asn Cys Pro Leu His Glu Lys Thr Lys Gly Met Phe
225                 230                 235                 240 aac aag gac ctc atc tct aag atg aag aag ggt tct tac ctc gtc aac   768
Asn Lys Asp Leu Ile Ser Lys Met Lys Lys Gly Ser Tyr Leu Val Asn
                245                 250                 255 acc gcc cgt ggc gcc atc gtt gtc aaa gag gac gtc gcc gct gcc ctc   816
Thr Ala Arg Gly Ala Ile Val Val Lys Glu Asp Val Ala Ala Ala Leu
            260                 265                 270 aag tct ggt cac ctc gcc ggt tac ggt ggt gat gtc tgg gac cac cag   864
Lys Ser Gly His Leu Ala Gly Tyr Gly Gly Asp Val Trp Asp His Gln
        275                 280                 285 ccc gct ccc aag gag cac cct ctg cga aac gcc aag aac aac tgg ggc   912
Pro Ala Pro Lys Glu His Pro Leu Arg Asn Ala Lys Asn Asn Trp Gly
    290                 295                 300 ggt ggt aat gcc atg gtt cct cac atg tct ggt acc tct ctg gat gct   960
Gly Gly Asn Ala Met Val Pro His Met Ser Gly Thr Ser Leu Asp Ala
305                 310                 315                 320
```

```
cag atc cga tac gcc aac ggt acc aag gct atc atc gac tct tac ctg     1008
Gln Ile Arg Tyr Ala Asn Gly Thr Lys Ala Ile Ile Asp Ser Tyr Leu
            325                 330                 335 tct ggt cgc cac gac tac aac cct cac gac ctc att gtc cac cag ggt     1056
Ser Gly Arg His Asp Tyr Asn Pro His Asp Leu Ile Val His Gln Gly
        340                 345                 350 gac tac gcc acc aag gct tat ggt cag cgt gag aag aaa tag             1098
Asp Tyr Ala Thr Lys Ala Tyr Gly Gln Arg Glu Lys Lys
    355                 360                 365

<210> SEQ ID NO 4
<211> LENGTH: 365
<212> TYPE: PRT
<213> ORGANISM: Gibberella zeae
<400> SEQUENCE: 4

Met Val Lys Val Leu Ala Val Leu Tyr Asp Gly Gly Gln His Ala Lys
1               5                   10                  15

Asp Gln Pro Leu Leu Leu Gly Thr Thr Glu Asn Glu Leu Gly Ile Arg
            20                  25                  30

Lys Trp Leu Glu Asp Gln Gly His Thr Leu Val Thr Thr Ser Asp Lys
        35                  40                  45

Asp Arg Glu Gly Ser Lys Phe Asp Glu Glu Leu Glu Asp Ala Glu Ile
    50                  55                  60

Ile Ile Thr Thr Pro Phe His Pro Gly Tyr Leu Thr Ala Glu Arg Leu
65                  70                  75                  80

Ala Lys Ala Lys Lys Leu Lys Leu Ala Val Thr Ala Gly Ile Gly Ser
                85                  90                  95

Asp His Val Asp Leu Asn Ala Ala Asn Lys Thr Asn Gly Gly Ile Thr
            100                 105                 110

Val Ala Glu Val Thr Gly Ser Asn Val Val Ser Val Ala Glu His Val
        115                 120                 125

Leu Met Thr Ile Leu Val Leu Ile Arg Asn Phe Val Pro Ala His Glu
    130                 135                 140

Gln Ile Glu Ala Gly Glu Trp Asp Val Ala His Ala Ala Lys Gln Glu
145                 150                 155                 160

Phe Asp Leu Glu Gly Lys Val Val Gly Thr Val Ala Val Gly Arg Ile
                165                 170                 175

Gly Glu Arg Val Leu Arg Arg Leu Lys Pro Phe Asp Cys Lys Glu Leu
            180                 185                 190

Leu Tyr Phe Asp Tyr Gln Pro Leu Ser Pro Glu Ala Glu Lys Glu Ile
        195                 200                 205

Gly Cys Arg Arg Val Asp Thr Leu Glu Glu Met Leu Ala Gln Cys Asp
    210                 215                 220

Ile Val Thr Ile Asn Cys Pro Leu His Glu Lys Thr Lys Gly Met Phe
225                 230                 235                 240

Asn Lys Asp Leu Ile Ser Lys Met Lys Lys Gly Ser Tyr Leu Val Asn
                245                 250                 255

Thr Ala Arg Gly Ala Ile Val Val Lys Glu Asp Val Ala Ala Ala Leu
            260                 265                 270

Lys Ser Gly His Leu Ala Gly Tyr Gly Gly Asp Val Trp Asp His Gln
        275                 280                 285

Pro Ala Pro Lys Glu His Pro Leu Arg Asn Ala Lys Asn Asn Trp Gly
    290                 295                 300

Gly Gly Asn Ala Met Val Pro His Met Ser Gly Thr Ser Leu Asp Ala
```

```
                    305                 310                 315                 320
            Gln Ile Arg Tyr Ala Asn Gly Thr Lys Ala Ile Ile Asp Ser Tyr Leu
                            325                 330                 335

Ser Gly Arg His Asp Tyr Asn Pro His Asp Leu Ile Val His Gln Gly
                            340                 345                 350

Asp Tyr Ala Thr Lys Ala Tyr Gly Gln Arg Glu Lys Lys
                            355                 360                 365

<210> SEQ ID NO 5
<211> LENGTH: 24
<212> TYPE: DNA
<213> ORGANISM: Artificial
<220> FEATURE:
<223> OTHER INFORMATION: Synthesized DNA

<400> SEQUENCE: 5
cgatcccgcg aaattaatac gact                                              24

<210> SEQ ID NO 6
<211> LENGTH: 24
<212> TYPE: DNA
<213> ORGANISM: Artificial
<220> FEATURE:
<223> OTHER INFORMATION: Synthesized DNA

<400> SEQUENCE: 6
tccggatata gttcctcctt tcag                                              24
```